United States Patent [19]

Riebel et al.

[11] Patent Number: 4,923,505

[45] Date of Patent: May 8, 1990

[54] SULPHONYLISO(THIO)UREAS

[75] Inventors: Hans-Jochem Riebel; Christa Fest, both of Wuppertal; Klaus-Helmut Müller, Duesseldorf; Hans-Joachim Santel, Leverkusen; Robert R. Schmidt, Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 242,398

[22] Filed: Sep. 9, 1988

[30] Foreign Application Priority Data

Sep. 16, 1987 [DE] Fed. Rep. of Germany ....... 3731053

[51] Int. Cl.$^5$ .................. C07D 251/18; C07D 251/46; C07D 251/16; A01N 43/66
[52] U.S. Cl. ...................................... 71/93; 544/211; 534/632
[58] Field of Search ........................... 71/93; 544/211; 534/632

[56] References Cited

U.S. PATENT DOCUMENTS 4,310,346 1/1982 Levitt et al. .......................... 544/208

FOREIGN PATENT DOCUMENTS

| | | |
|---|---|---|
| 0005986 | 12/1979 | European Pat. Off. . |
| 0030433 | 6/1981 | European Pat. Off. . |
| 0107624 | 5/1984 | European Pat. Off. . |
| 0112289 | 6/1984 | European Pat. Off. . |
| 3517844 | 3/1986 | Fed. Rep. of Germany . |
| 3634927 | 4/1988 | Fed. Rep. of Germany . |

OTHER PUBLICATIONS

Chemical Abstracts, vol. 98, No. 9, 2/28/83, Columbus, Ohio, U.S.A. Merchan, F. L. et al., "Synthesis of 2-Sulfonylaminobenzimidazoles . . . Dichloromethylenesulfonamides", p. 623, Col. 2, paragraph No. 72 002y & Synthesis 1982, (11), 984–6.
Chemical Abstracts, vol. 67, No. 21, 11/20/67, Columbus, Ohio, U.S.A. E. Kuehle et al., "Synthesis of Diahalo Isocyanides", p. 9378, Col. 1, Paragraph No. 99 821m & Agnew. Chem. 79 (15), 663–80 (1967).
Chemical Abstracts, vol. 78, No. 17, 4/30/73, Columbus, Ohio, U.S.A., Gordienko, N. S. et al., "Tautomerism and Acid Properties of Acyl Derivatives . . . Ethers", p. 412, Col. 1, paragraph No. 110 398d & Zzv. Ucheb. Zaved., Khim. Kim. Teknol. 1972, 15 (10), 1535–8.
Chemical Abstracts, vol. 77, No. 9, 8/28/72, Columbus, Ohio, U.S.A. Markov, V. I. et al., "Alkylation of Disodium Salts of Arylsulfimidodithiocarbonic Acid", p. 457, Col. 2, paragraph No. 61 443h & Khim. Tekhnol. (Kharkov) 1971, No. 24, 23–6.
Chemical Abstracts, vol. 83, No. 21, 11/24/75, Columbus, Ohio, U.S.A. Dubina, V. L. et al., "Arylsulfonyl-benzimidoyl Chlorides., IX., Synthesis of Mixed Anhydrides of N–(Arylsulfonyl) Imidobenzoic and Certain Carboxylic Acids", p. 523, Col. 1, paragraph, No. 178 491n & Zh. Org. Khim. 1975, 11(8), 1724–7.

Primary Examiner—John M. Ford
Attorney, Agent, or Firm—Sprung Horn Kramer & Woods

[57] ABSTRACT

Herbicidal sulphonyliso(thio)ureas of the formula

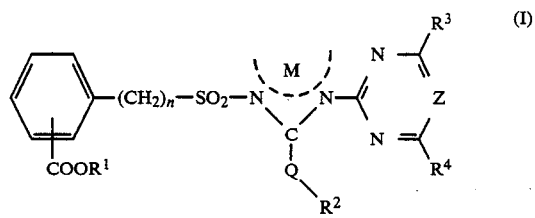

in which

M stands for hydrogen or an alkali metal equivalent or an alkaline earth metal equivalent, n stands for the numbers zero or 1, Q stands for oxygen or sulphur, $R^1$ stands for $C_1$–$C_6$-alkyl which is optionally substituted by substituents from the series comprising halogen or $C_1$–$C_4$-alkoxy, $R^2$ stands for an optionally substituted phenyl radical, $R^3$ stands for $C_1$–$C_2$-alkyl or $C_1$–$C_2$-alkoxy which are optionally substituted by halogen, $R^4$ stands for $C_1$–$C_2$-alkyl or $C_1$–$C_2$-alkoxy which are optionally substituted by halogen, and Z stands for N or CH, with the proviso that Z stands for N when n stands for zero.

Intermediates of the formula

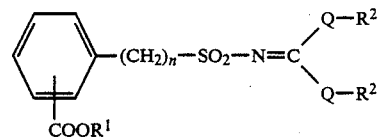

and

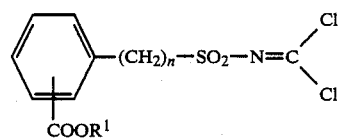

are also new.

10 Claims, No Drawings

SULPHONYLISO(THIO)UREAS

The invention relates to new sulphonyliso(thio)-ureas and an inventive process and new intermediates for their preparation, and their use as herbicides.

It is known that certain sulphonylisoureas, such as, for example, N'-(2-methoxycarbonyl-phenylsulphony)-N"-(4,6-dimethoxy-pyrimidin-2-yl)-O-phenylisourea, exhibit herbicidal properties (compare EP-A 173,957). The action of these compounds and the course of the known process for their preparation via corresponding sulphonylguanidines are not wholly satisfactory in all cases, however.

New sulphonyliso(thio)ureas of the general formula (I)

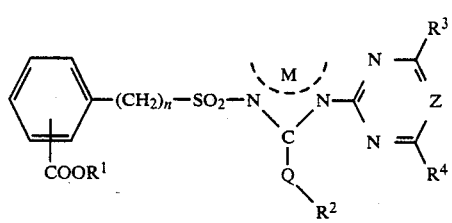

in which

M stands for hydrogen or an alkali metal equivalent or an alkaline earth metal equivalent, n stands for the numbers zero or 1, Q stands for oxygen or sulphur, $R^1$ stands for $C_1-C_6$-alkyl which is optionally substituted by substituents from the series comprising halogen or $C_1-C_4$-alkoxy, $R^2$ stands for a phenyl radical, which is optionally substituted by one or more radicals from the series comprising halogen [such as fluorine, chlorine, bromine and iodine in particular], cyano, nitro, hydroxyl, carboxyl, $C_1-C_6$-alkyl [which is optionally substituted by fluorine, chlorine, bromine, nitro, cyano, hydroxyl, carboxyl, $C_1-C_4$-alkoxy-carbonyl, $C_1-C_4$-alkoxy, $C_1-C_4$-alkylthio or phenyl], $C_3-C_6$-cycloalkyl, $C_1-C_4$-alkoxy [which is optionally substituted by fluorine, chlorine, bromine, cyano, carboxyl, $C_1-C_4$-alkoxy, $C_1-C_4$-alkylthio or $C_1-C_4$-alkoxy-carbonyl], $C_1-C_4$-alkylthio [which is optionally substituted by fluorine, chlorine, bromine, cyano, carboxyl, $C_1-C_4$-alkoxy-carbonyl], amino, $C_1-C_4$-alkyl-amino or di-($C_1-C_4$-alkyl)-amino [which are optionally substituted by fluorine, chlorine, bromine, cyano, carboxyl, $C_1-C_4$-alkoxy or $C_1-C_4$-alkoxy-carbonyl], $C_1-C_4$-alkyl-carbonyl-amino, $C_1-C_4$-alkoxy-carbonylamino, (di)-$C_1-C_4$-alkylamino-carbonylamino, formyl, $C_1-C_4$-alkyl-carbonyl, benzoyl, $C_1-C_4$-alkoxy-carbonyl, phenoxy-carbonyl, benzyloxycarbonyl, phenyl [which is optionally substituted by fluorine, chlorine, bromine, cyano, nitro, hydroxyl or methyl], phenoxy, phenylthio, phenylsulphonyl, phenylamino or phenylazo [which are optionally substituted by fluorine, chlorine, bromine, cyano, nitro, methyl and/or trifluoromethyl], pyridoxy or pyrimidoxy [which are optionally substituted by fluorine, chlorine, bromine, cyano, nitro, methyl and/or trifluoromethyl], $C_1-C_4$-alkyl-carbonyloxy, $C_1-C_4$-alkoxy-carbonyloxy, $C_1-C_4$-alkyl-amino-carbonyloxy and di-($C_1-C_4$-alkyl)-amino-carbonyloxy, or which is optionally anellated by an alkylene chain [which is optionally branched and/or interrupted by one or more oxygen atoms] or a benzene radical [which is optionally substituted by fluorine, chlorine, bromine, cyano, nitro, methyl and/or trifluoromethyl];

$R^3$ stands for $C_1-C_2$-alkyl or $C_1-C_2$-alkoxy which are optionally substituted by halogen, $R^4$ stands for $C_1-C_2$-alkyl or $C_1-C_2$-alkoxy which are optionally substituted by halogen, and Z stands for N or CH, with the proviso that Z stands for N when n stands for zero have now been found.

Additionally, an inventive process for the preparation of the new sulphonyliso(thio)ureas of the general formula (I) has been found, which is characterized in that N-sulphonyl-imino-(dithio)carbonic acid diesters of the general formula (II)

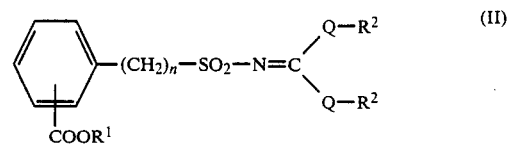

in which n, Q, $R^1$ and $R^2$ have the abovementioned meanings, are reacted with amino compounds of the general formula (III)

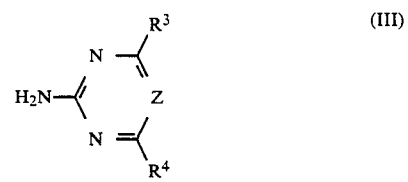

in which $R^3$, $R^4$ and Z have the abovementioned meanings, or with alkali metal salts or alkaline earth metal salts thereof in the presence of a diluent and if appropriate in the presence of a basic metal compound, at temperatures between 0° C. and 100° C.

Surprisingly, the compounds of the formula (I) can be obtained in high yields and in good quality by the preparation process according to the invention, for it had been expected that the carboxylate ester group present in the starting substances of the formula (II) and in the products of the formula (I) would enter into undesirable reactions with the amino compounds of the formula (III).

The new sulphonyliso(thio)ureas of the general formula (I) are distinguished by strong herbicidal activity.

Surprisingly, the new compounds of the formula (I) show considerably better herbicidal action than previously known sulphonylisoureas with the same type of action.

The invention relates preferably to compounds of the formula (I) in which

M stands for hydrogen or a sodium, potassium, magnesium or calcium equivalent, n stands for the numbers zero or 1, Q stands for oxygen or sulphur, $R^1$ stands for methyl, ethyl, propyl, isopropl, butyl, isobutyl, sec.-butyl, 2-fluoro-ethyl, 2-chloro-ethyl, 2-methoxy-ethyl or 2-ethoxyethyl, $R^2$ stands for a phenyl radical, which is optionally substituted by one or two radicals from the series comprising fluorine, chlorine, bromine, iodine, cyano, nitro, hydroxyl, carboxyl, $C_1$-$C_3$-alkoxy-carbonyl, $C_1$-$C_4$-alkyl, trifluoromethyl, hydroxymethyl, methoxycarbonylmethyl, phenyl-$C_1$-$C_3$-alkyl, cyclohexyl, $C_1$-$C_3$-alkoxy, trifluoromethoxy, $C_1$-$C_3$-alkylthio, trifluoromethylthio, dimethylamino, amino, acetamido, methylaminocarbonyl, formyl, acetyl, benzoyl, phenyl, hydroxyphenyl, phenoxy [which is optionally substituted by chlorine and/or trifluoromethyl], phenylamino, phenylazo, pyridoxy [which is optionally substituted by chlorine and/or trifluoromethyl], or which is optionally benzanellated;

$R^3$ stands for methyl, ethyl, trifluoromethyl, methoxy, ethoxy, difluoromethoxy or trifluoroethoxy, $R^4$ stands for methyl, methoxy, ethoxy, difluoromethoxy or trifluoroethoxy, and Z stands for N or CH with the proviso that Z stands for N when n stands for zero.

The invention relates in particular to compounds of the formula (I) in which

M stands for hydrogen,
n stands for zero,
Q stands for sulphur,
$R^1$ stands for methyl or ethyl,
$R^2$ stands for phenyl which is optionally substituted by a substituent from the series comprising fluorine, chlorine, methyl or methoxy,
$R^3$ stands for methyl or methoxy,
$R^4$ stands for methoxy, and
Z stands for N, with the proviso that the $COOR^1$ group is situated in the ortho-position.

The invention additionally relates in particular to compounds of the formula (I) in which M stands for hydrogen,
n stands for 1,
Q stands for sulphur,
$R^1$ stands for methyl or ethyl,
$R^2$ stands for phenyl which is optionally substituted by a substituent from the series comprising fluroine, chlorine, methyl or methoxy,
$R^3$ stands for methyl, ethyl, trifluoromethyl, methoxy or difluoromethoxy,
$R^4$ stands for methoxy or difluoromethoxy, and
Z stands for CH, with the proviso that the $COOR^1$ group is situated in the ortho-position.

If, for example, diphenyl N-(2-methoxycarbonyl-phenylsulphonyl)-imino-carbonate and the potassium salt of 2-amino-4,6-dimethoxy-s-triazine are used as starting materials, then the course of the reaction in the process according to the invention can be represented by the following equation:

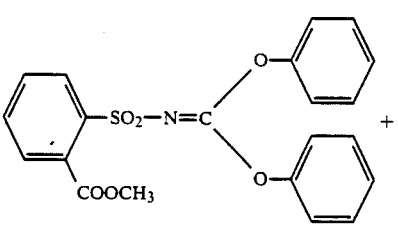

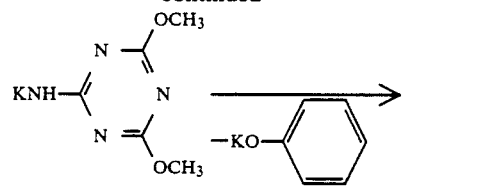

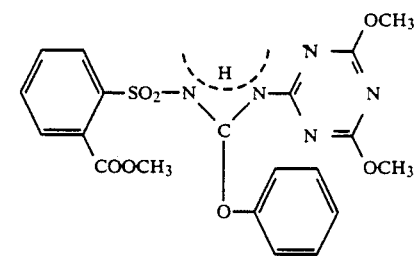

Formula (II) provides a general definition of the N-sulphonyl-imino-(dithio)carbonic acid diesters to be used as starting materials in the process according to the invention. In formula (II), n, Q, $R^1$ and $R^2$ preferably or particularly have the same meanings as they are preferably or particularly preferably given above in the scope of the definition of the substituents of the formula (I).

Examples of the starting materials of the formula (II) are shown in Table 1 below.

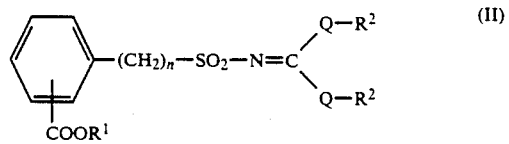

TABLE 1

| \multicolumn{5}{c}{Examples of the starting materials of the formula (II)} |
| n | Q | $R^1$ | $R^2$ | Position $COOR^1$ |
| --- | --- | --- | --- | --- |
| 0 | O | $CH_3$ | ⌬ | ortho |
| 0 | O | $C_2H_5$ | ⌬ | ortho |
| 0 | S | $CH_3$ | ⌬ | ortho |
| 0 | S | $C_2H_5$ | ⌬ | ortho |
| 1 | O | $CH_3$ | ⌬ | ortho |

TABLE 1-continued

| | | | Examples of the starting materials of the formula (II) | |
|---|---|---|---|---|
| n | Q | R¹ | R² | Position COOR¹ |
| 1 | O | C₂H₅ | phenyl | ortho |
| 1 | S | CH₃ | phenyl | ortho |
| 1 | S | C₂H₅ | phenyl | ortho |
| 0 | O | CH₃ | 4-F-phenyl | ortho |
| 0 | O | CH₃ | 4-F-phenyl | ortho |
| 0 | O | C₂H₅ | 4-F-phenyl | ortho |
| 0 | S | C₂H₅ | 4-F-phenyl | ortho |
| 0 | O | CH₃ | 4-Cl-phenyl | ortho |
| 0 | S | CH₃ | 4-Cl-phenyl | ortho |
| 0 | O | CH₃ | 4-CH₃-phenyl | ortho |
| 0 | S | CH₃ | 4-CH₃-phenyl | ortho |
| 0 | O | CH₃ | 4-OCH₃-phenyl | ortho |
| 0 | S | CH₃ | 4-OCH₃-phenyl | ortho |
| 0 | O | CH₃ | phenyl | meta |
| 0 | O | CH₃ | phenyl | para |
| 0 | O | C₂H₅ | phenyl | para |
| 0 | S | CH₃ | 4-OH-phenyl | ortho |
| 1 | S | CH₃ | 4-OH-phenyl | ortho |
| 0 | O | CH₃ | 3,4-Cl₂-phenyl | ortho |
| 0 | S | CH₃ | 3,4-Cl₂-phenyl | ortho |
| 0 | O | CH₃ | 4-OCH₃-phenyl | para |
| 0 | S | C₂H₅ | 4-OH-phenyl | ortho |
| 0 | O | CH₃ | 3,4-(CH₃)₂-phenyl | ortho |
| 0 | O | CH₃ | 3,5-(CH₃)₂-phenyl | ortho |

TABLE 1-continued

| | | Examples of the starting materials of the formula (II) | | |
|---|---|---|---|---|
| n | Q | R¹ | R² | Position COOR¹ |
| 0 | O | C₂H₅ | 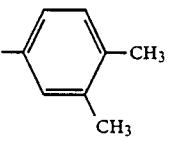 2,3-dimethylphenyl | ortho |
| 0 | O | C₂H₅ | 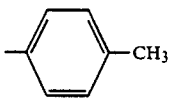 3-methylphenyl | ortho |
| 0 | S | C₂H₅ | 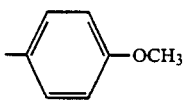 4-methoxyphenyl | ortho |

The N-sulphonyl-imino-(dithio)carbonic acid diesters of the formula (II) were hitherto unknown from the literature. The compounds of the formula (II) are obtained when sulphonyl-isocyanide dichlorides of the general formula (IV)

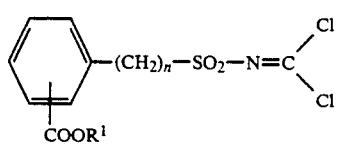

in which n and R¹ have the abovementioned meanings, are reacted with compounds of the formula (V)

M—Q—R²    (V)

in which

M, Q and R² have the abovementioned meanings, in the presence of a diluent, such as, for example, toluene, and if appropriate in the presence of an acid acceptor, such as, for example, triethylamine, at temperatures between 0° C. and 50° C., and worked up by customary methods.

In the starting substances of the formula (V), M, Q and R² preferably or particularly preferably have the same meanings as they are preferably or particularly given above in the scope of the definition of the substituents of the formula (I). Examples for the compounds of the formula (V) which may be mentioned are: phenol, thiophenol, 4-fluoro-phenol and -thiophenol, 4-chloro-phenol and -thiophenol, 4-methyl-phenol and -thiophenol, 4-hydroxy-phenol and -thiophenol, 4-methoxy-phenol and -thiophenol, and 3,4-dimethyl-phenol and -thiophenol.

The compounds of the formula (V) are known synthesis chemicals.

In the starting materials of the formula (IV), n and R¹ preferably or particularly have the same meanings as they are preferably or particularly preferably given above in the scope of the definition of the substituents of the formula (I).

Examples of the starting materials of the formula (IV) are shown in Table 2 below.

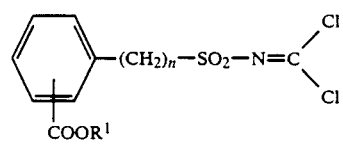

TABLE 2

| Examples of the starting materials of the formula (IV) | | |
|---|---|---|
| n | R¹ | Position COOR¹ |
| 0 | CH₃ | ortho |
| 1 | CH₃ | ortho |
| 0 | C₂H₅ | ortho |
| 1 | C₂H₅ | ortho |
| 0 | CH₃ | meta |
| 0 | CH₃ | para |
| 0 | C₂H₅ | para |

The compounds of the formula (IV) were hitherto unknown from the literature. The sulphonyl-isocyanide dichlorides of the formula (IV) are obtained when dimethyl N-sulphonyl-imino-dithiocarbonate of the formula (VI)

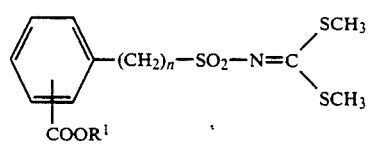

in which n and R have the abovementioned meanings, are reacted with chlorine or sulphuryl chloride, if appropriate in the presence of a diluent, such as, for example, methylene chloride, chloroform or tetrachloromethane, at temperatures between 30° C. and 70° C., and then distilled.

In the starting materials of the formula (VI), n and R¹ preferably or particularly have the same meanings as they are preferably or particularly preferably given above in the scope of the definition of the substituents of the formula (I).

Examples of the starting materials of the formula (VI) are shown in Table 3 below.

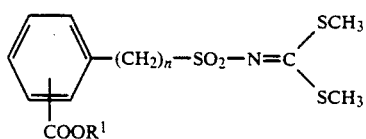

TABLE 3

| Examples of the starting materials of the formula (VI) | | |
|---|---|---|
| n | R¹ | Position COOR¹ |
| 0 | CH₃ | ortho |
| 1 | CH₃ | ortho |
| 0 | C₂H₅ | ortho |
| 1 | C₂H₅ | ortho |
| 0 | CH₃ | meta |
| 0 | C₂H₅ | meta |
| 0 | CH₃ | para |
| 0 | C₂H₅ | para |

The dimethyl N-sulphonyl-imino-dithiocarbonates of the formula (VI) are known - with the synonym isodithiocarbamic acid derivatives, such as, for example, N-(2-methoxycarbonyl-benzenesulphonyl)- and N-(2-ethoxycarbonyl-benzenesulphonyl-S,S-dimethyl-isodithiocarbamic acid esters -and/or can be prepared by processes which are known per se (compare EP-A 121,082).

The dimethyl N-sulphonyl-imino-dithiocarbonates of the formula (VI) are also obtained by an inventive process, which is the subject of a previously unpublished DE-patent application, by reacting dimethyl imino-dithiocarbonate or its hydrochloride with sulphonyl halides of the formula (VII)

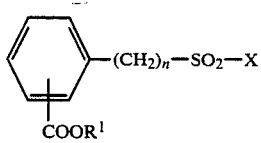

in which
n and $R^1$ have the abovementioned meanings and
X stands for halogen, preferably for chlorine, in the presence of an acid acceptor, such as, for example, 1,4-diazabicyclo-[2,2,2]-octane (DABCO), and in the presence of a diluent, such as, for example, methylene chloride, at temperatures between $-20°$ C. and $+50°$ C., and worked up by customary methods (cf. German Pat.Appln.P 3726424.9 of 8/8/87).

Dimethyl iminodithiocarbonates and the sulphonyl halides of the formula (VII) are known (compare DE-AS (German Published Specification) 1,252,656 or DE-OS (German Published Specification) 3,431,920; Chem. Ber. 90 (1957), 841–852; J. Org. Chem. 27 (1962), 1703–1709).

Formula (III) provides a general definition of the amino compounds furthermore to be used as starting materials in the process according to the invention for the preparation of the new sulphonyliso(thio)ureas. In formula (III), $R^3$, $R^4$ and Z preferably or particularly have the same meanings as they are preferably or particularly given above in the scope of the definition of the substituents of the formula (I).

Examples of the starting materials of the formula (III) are shown in Table 4 below.

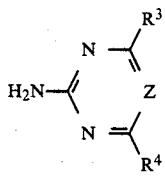

TABLE 4

| \multicolumn{6}{c}{Examples of the starting materials of the formula (III)} |
| $R^3$ | $R^4$ | Z | $R^3$ | $R^4$ | Z |
|---|---|---|---|---|---|
| $CH_3$ | $CH_3$ | CH | $OC_2H_5$ | $OC_2H_5$ | CH |
| $CH_3$ | $OCH_3$ | CH | $CF_3$ | $CH_3$ | CH |
| $OCH_3$ | $OCH_3$ | CH | $CF_3$ | $OCH_3$ | CH |
| $C_2H_5$ | $OCH_3$ | CH | $CF_3$ | $OC_2H_5$ | CH |
| $CH_3$ | $OC_2H_5$ | CH | $CF_3$ | $OCHF_2$ | CH |
| $OCH_3$ | $OCHF_2$ | CH | $CH_3$ | $OCHF_2$ | CH |
| $OCHF_2$ | $OCHF_2$ | CH | $C_2H_5$ | $OCHF_2$ | CH |
| $CH_3$ | $CH_3$ | N | $CH_3$ | $OCH_3$ | N |
| $OCH_3$ | $OCH_3$ | N | $C_2H_5$ | $OCH_3$ | N |
| $CH_3$ | $OC_2H_5$ | N | $OC_2H_5$ | $OC_2H_5$ | N |

The compounds of hte formula (III) are known and/or can be prepared by processes which are known per se (compare EP-A 121,082, EP-A 125,205, EP-A 126,711, EP-A 152,378 and U.S. Pat. No. 4,299,960).

Alkali metal salts or alkaline earth metal salts thereof can be prepared in a customary manner by reaction with basic metal compounds, such as, for example, hydrides of sodium, potassium, magnesium or calium, and also sodium tert.-butylate or potassium tert.-butylate.

The process according to the invention for the preparation of the new sulphonyliso(thio)ureas of the formula (I) is carried out using diluents. Suitable diluents in this case are practically all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimetyl ether and diglycol dimethyl ether, tetrahydrofuran and dioxane, ketones such as acetone, methyl ethyl ketone, methyl isopropyl ketone, and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylenesulphone and hexamethylphosphoric triamide.

Ethers, such as, for example, diethyl ether and dibutyl ether, glycol dimethyl ether and diglycol dimethyl ether, tetrahydrofuran and dioxane, are very particularly preferably used as diluents in the process according to the invention.

In the process according to the invention, all customary basic metal compounds can be employed. Preferably suitable are alkali metal hydrides, such as, for example, lithium hydride, sodium hydride and potassium hydride, alkaline earth metal hydrides, such as, for example, calcium hydride, alkali metal hydroxides such as, for example, sodium hydroxide and potassium hydroxide, alkaline earth metal hydroxides such as, for example, calcium hydroxide, and alkali metal carbonates and alkali metal alcoholates such as sodium carbonate and potassium carbonate, and sodium tert.-butylate and potassium tert.-butylate.

Sodium tert.-butylate and potassium tert.-butylate are very particularly preferably employed as basic metal compounds in the process according to the invention.

The reaction temperatures can be varied within a substantial range in the process according to the invention. In general, the process is carried out at temperatures between $0°$ C. and $100°$ C., preferably at temperatures between $10°$ C. and $60°$ C.

The process according to the invention is generally carried out under atmospheric pressure. However, it is also possible to work at elevated or reduced pressure.

For carrying out the process according to the invention, between 0.5 and 2 moles, preferably between 0.8 and 1.2 moles, of amino compound of the formula (III) or of its alkali metal salts or alkaline earth metal salts are generally employed per mol of N-sulphonyl-imino-(dithio)carbonic acid diester of the formula (II).

For carrying out the process according to the invention, the reaction components can be mixed in an arbitrary sequence and can be worked up after completion of the reaction by customary methods.

In a preferred embodiment of the process according to the invention, the amino compound of the formula (III) is first reacted with a suitable basic metal compound in a diluent. The N-sulphonyl-imino-(dithio)carbonic acid diester of the formula (II) is then added to it and the reaction mixture is stirred until the end of the reaction. For working up, the mixture is diluted with water and acidified with a strong acid, such as, for example, hydrochloric acid, and extracted with a practically water-immiscible organic solvent, such as, for example, methylene chloride, and the organic phase is washed using water, dried and then concentrated under reduced pressure. The residue essentially contains the product of the formula (I). It can be brought to crystallization by customary methods, for example by trituration with an organic solvent, such as, for example, ethanol, and can be isolated by filtration with suction.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and railway tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hop fields, and for the selective combating of weeds in annual cultures.

The active compounds according to the invention can be employed for selectively combating weeds in wheat, barley and rice in particular, and partly also in corn and soy beans, preferably by the post-emergence method.

The active compounds can be converted into the customary formulations, such as solutions, emulsions, wettable powders, suspensions, powders, dusting agents, pastes, soluble powders, granules, suspension-/emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emulsifiers, such as polyoxyethylene fatty acid esters, polyoxethylene fatty alcohol ethers, for example alkylaryl polyglycol ethers, alkylsulphonates, alkyl sulphates, arylsulphonates as well as albumin hydrolysis products; as dispersing agents there are suitable: for example lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in their formulations, can also be used, for combating weeds, as mixtures with known herbicides, finished formulations or tank mixes being possible.

Suitable components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beets, 4-amino-6-(1,1-dimethylethyl)-3-methylthio-1,2,4-triazin-5(4H)-one for combating weeds in soy beans. Some mixtures surprisingly also exhibit a synergistic effect.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and graules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

Example 1

A mixture of 4.6 g (0.033 mol) of 2-amino-4-methoxy-6-methyl-s-triazine, 2 g of sodium hydride and 150 ml of tetrahydrofuran is stirred at 20° C. for 24 hours. 14.8 g (0.033 mol) of diphenyl N-(2-methoxycarbonyl-phenyl-sulphonyl)-imino-dithiocarbonate are then added to it in portions and the reaction mixture is stirred at 20° C. for 18 hours. After diluting with 300 ml of water, the mixture is acidified using 2N-hydrochloric acid and extracted using methylene chloride. The methylene chloride solution is washed with water, dried using sodium sulphate and filtered. The solvent and the thiophenol are removed from the filtrate by distillation under reduced pressure. The residue is stirred with ethanol and the crystalline precipitated product is isolated by filtering with suction.

11.0 g (71% of theory) of N'-(4-methoxy-6-methyl-s-triazin-2-yl)-N'-(2-methoxycarbonyl-phenylsulphonyl)-S-phenyl-isothiourea of melting point 139° C. are obtained.

The compounds of the formula (I)

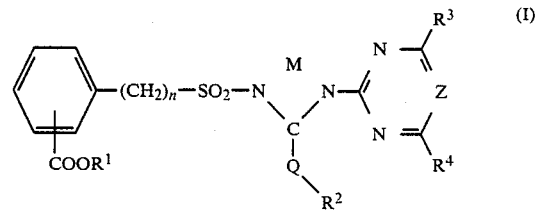

shown in Table 5 below can be prepared analogously to Example 1 and in accordance with the general description of the process according to the invention.

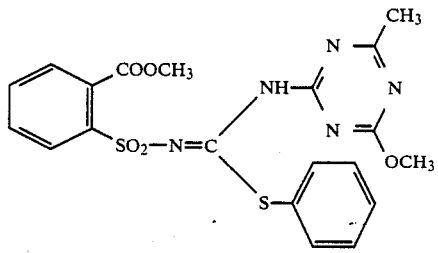

TABLE 5

Examples of the compounds of the formula (I)
The COOR¹ group is situated in the ortho-position.

| Example No. | n | Q | R¹ | R² | R³ | R⁴ | M | Z | Melting point (°C.) |
|---|---|---|---|---|---|---|---|---|---|
| 2 | 0 | S | $CH_3$ | —⟨C₆H₄⟩—OH | $CH_3$ | $OCH_3$ | H | N | 116 |
| 3 | 0 | S | $CH_3$ | —⟨C₆H₄⟩—$OCH_3$ | $CH_3$ | $OCH_3$ | H | N | 134 |
| 4 | 0 | S | $CH_3$ | —⟨C₆H₄⟩—F | $CH_3$ | $OCH_3$ | H | N | 123 |

TABLE 5-continued
Examples of the compounds of the formula (I)
The COOR¹ group is situated in the ortho-position.
| Example No. | n | Q | R¹ | R² | R³ | R⁴ | M | Z | Melting point (°C.) |
|---|---|---|---|---|---|---|---|---|---|
| 5 | 0 | S | CH₃ | 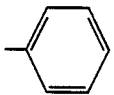 | CH₃ | OCH₃ | Na | N | |
| 6 | 0 | S | CH₃ | 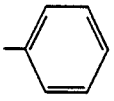 | CH₃ | OCH₃ | K | N | |
| 7 | 0 | S | CH₃ | 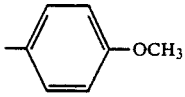 | CH₃ | OCH₃ | ½Ca | N | |
| 8 | 0 | S | CH₃ | 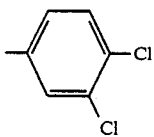 | CH₃ | OCH₃ | H | N | 146 |
| 9 | 0 | S | CH₃ | 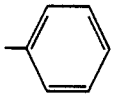 | OCH₃ | OCH₃ | H | N | |
| 10 | 0 | S | CH₃ | 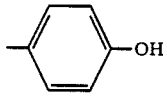 | OCH₃ | OCH₃ | H | N | |
| 11 | 0 | S | CH₃ | 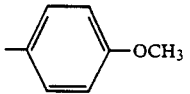 | OCH₃ | OCH₃ | H | N | |
| 12 | 0 | S | CH₃ | 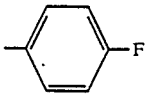 | OCH₃ | OCH₃ | H | N | |
| 13 | 0 | S | CH₃ | 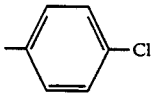 | OCH₃ | OCH₃ | H | N | |
| 14 | 0 | S | CH₃ | 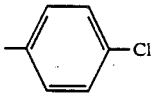 | CH₃ | OCH₃ | H | N | |
| 15 | 0 | S | CH₃ | 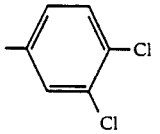 | OCH₃ | OCH₃ | H | N | |
| 16 | 0 | O | CH₃ | 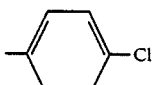 | CH₃ | OCH₃ | H | N | |

TABLE 5-continued

Examples of the compounds of the formula (I)
The COOR¹ group is situated in the ortho-position.

| Example No. | n | Q | R¹ | R² | R³ | R⁴ | M | Z | Melting point (°C.) |
|---|---|---|---|---|---|---|---|---|---|
| 17 | 0 | O | CH₃ | 4-Cl-phenyl | OCH₃ | OCH₃ | H | N | |
| 18 | 1 | S | CH₃ | 4-OH-phenyl | OCH₃ | OCH₃ | H | CH | 175 |
| 19 | 1 | S | CH₃ | phenyl | CH₃ | OCH₃ | H | CH | |
| 20 | 1 | O | CH₃ | 4-F-phenyl | OCH₃ | OCH₃ | H | CH | |
| 21 | 1 | O | CH₃ | 4-Cl-phenyl | CH₃ | OCH₃ | H | CH | |
| 22 | 1 | S | CH₃ | 4-OCH₃-phenyl | OCH₃ | OCH₃ | H | CH | |
| 23 | 1 | S | CH₃ | 4-OCH₃-phenyl | OCH₃ | OCH₃ | K | CH | |
| 24 | 1 | O | CH₃ | phenyl | CF₃ | OCH₃ | H | CH | |
| 25 | 0 | S | C₂H₅ | 4-OH-phenyl | CH₃ | OCH₃ | H | N | |
| 26 | 0 | S | C₂H₅ | phenyl | OCH₃ | OCH₃ | H | N | |
| 27 | 0 | S | C₂H₅ | 4-OCH₃-phenyl | OCH₃ | OCH₃ | H | N | |
| 28 | 0 | S | C₂H₅ | 4-OCH₃-phenyl | CH₃ | OCH₃ | H | N | |
| 29 | 0 | S | C₂H₅ | 4-F-phenyl | CH₃ | OCH₃ | H | N | |

TABLE 5-continued

Examples of the compounds of the formula (I)
The COOR¹ group is situated in the ortho-position.

| Example No. | n | Q | R¹ | R² | R³ | R⁴ | M | Z | Melting point (°C.) |
|---|---|---|---|---|---|---|---|---|---|
| 30 | 0 | S | $C_2H_5$ | 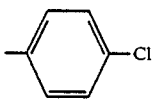 4-Cl-phenyl | $OCH_3$ | $OCH_3$ | H | N | |
| 31 | 0 | S | $C_2H_5$ | 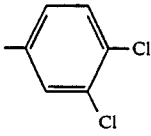 3,4-diCl-phenyl | $OCH_3$ | $OCH_3$ | H | N | |
| 32 | 0 | S | $C_2H_5$ | 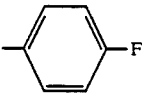 4-F-phenyl | $OCH_3$ | $OCH_3$ | H | N | |
| 33 | 0 | S | $C_2H_5$ | 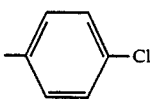 4-Cl-phenyl | $CH_3$ | $OCH_3$ | H | N | |
| 34 | 0 | S | $C_2H_5$ | 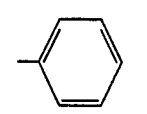 phenyl | $CH_3$ | $OCH_3$ | H | N | |
| 35 | 1 | S | $C_2H_5$ | 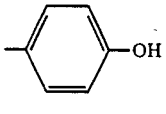 4-OH-phenyl | $OCH_3$ | $OCH_3$ | H | CH | |
| 36 | 1 | S | $C_2H_5$ | 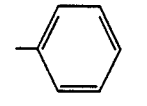 phenyl | $OCH_3$ | $OCH_3$ | H | CH | |
| 37 | 1 | S | $C_2H_5$ | 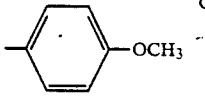 4-OCH₃-phenyl | $CH_3$ | $OCH_3$ | H | CH | |
| 38 | 1 | S | $C_2H_5$ | 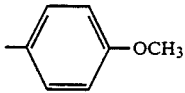 4-OCH₃-phenyl | $OCH_3$ | $OCH_3$ | H | CH | |
| 39 | 1 | S | $C_2H_5$ | 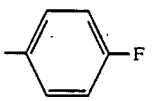 4-F-phenyl | $OCH_3$ | $OCH_3$ | H | CH | |
| 40 | 1 | S | $C_2H_5$ | 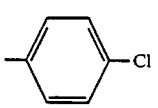 4-Cl-phenyl | $OCH_3$ | $OCH_3$ | H | CH | |
| 41 | 0 | O | $CH_3$ | 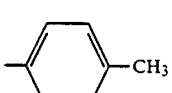 4-CH₃-phenyl | $CH_3$ | $OCH_3$ | H | N | |

TABLE 5-continued
Examples of the compounds of the formula (I)
The COOR¹ group is situated in the ortho-position.
| Example No. | n | Q | R¹ | R² | R³ | R⁴ | M | Z | Melting point (°C.) |
|---|---|---|---|---|---|---|---|---|---|
| 42 | 0 | O | CH₃ | 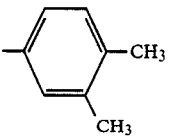 | CH₃ | OCH₃ | H | N | |
| 43 | 0 | O | CH₃ | 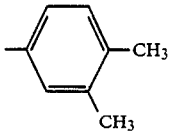 | OCH₃ | OCH₃ | H | N | |
| 44 | 0 | O | CH₃ | 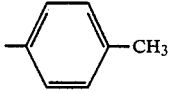 | OCH₃ | OCH₃ | H | N | |
| 45 | 0 | O | CH₃ | 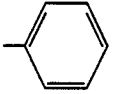 | OCH₃ | OCH₃ | H | N | |
| 46 | 0 | O | CH₃ | 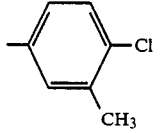 | OCH₃ | OCH₃ | H | N | |
| 47 | 0 | O | CH₃ | 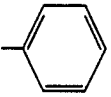 | CH₃ | OCH₃ | H | N | |
| 48 | 0 | S | CH₃ | 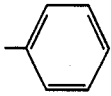 | CH₃ | OC₂H₅ | H | N | |
| 49 | 0 | O | CH₃ | 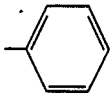 | CH₃ | OC₂H₅ | H | N | |
| 50 | 0 | S | CH₃ | 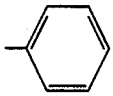 | C₂H₅ | OCH₃ | H | N | |
| 51 | 0 | O | CH₃ | 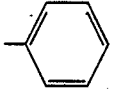 | C₂H₅ | OCH₃ | H | N | |
| 52 | 0 | O | C₂H₅ | 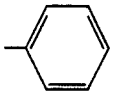 | CH₃ | OCH₃ | H | N | |
| 53 | 0 | O | C₂H₅ | 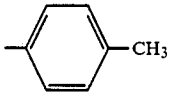 | CH₃ | OCH₃ | H | N | |

TABLE 5-continued

Examples of the compounds of the formula (I)
The COOR¹ group is situated in the ortho-position.

| Example No. | n | Q | R¹ | R² | R³ | R⁴ | M | Z | Melting point (°C.) |
|---|---|---|---|---|---|---|---|---|---|
| 54 | 0 | O | C₂H₅ | 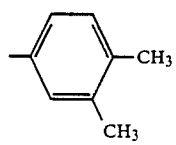 2,3-dimethylphenyl | CH₃ | OCH₃ | H | N | |
| 55 | 0 | O | C₂H₅ | 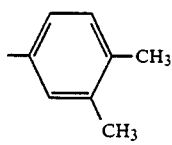 2,3-dimethylphenyl | OCH₃ | OCH₃ | H | N | |
| 56 | 1 | O | CH₃ | 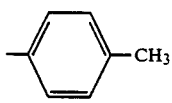 4-methylphenyl | OCH₃ | OCH₃ | H | CH | |

Starting materials of the formula (II)

Example (II-1)

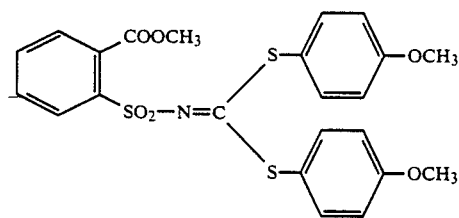

A solution of 7.4 g (0.05 mol) of N-(2-methoxycarbonyl-phenylsulphonyl)-isocyanide dichloride in 75 ml of toluene is added dropwise at 22° C. with stirring to a mixture of 14.0 g (0.10 mol) of 4-methoxy-thiophenol, 10.0 g (0.10 mol) of triethylamine and 100 ml of toluene. The reaction mixture is stirred at 22° C. for 18 hours and then shaken with 200 ml of water. The organic phase is separated off, dried using sodium sulphate and filtered. The filtrate is concentrated, the residue is triturated with ethanol and the crystalline precipitated product is isolated by filtering with suction.

16.6 g (66% of theory) of S,S-bis-(4-methoxy-phenyl) N-(2-methoxycarbonyl-phenylsulphonyl)-imino-dithiocarbonate of melting point 101° C. are obtained.

The compounds of the formula (II)

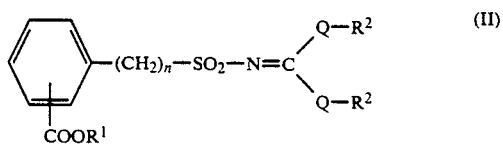

shown in Table 6 below - and also the compounds shown in Table 1 - can be prepared analogously to Example (II-1).

TABLE 6

Examples of the compounds of the formula (II)

| Example No. | n | Q | R¹ | R² | Position COOR¹ | Melting point (°C.) |
|---|---|---|---|---|---|---|
| II-2 | O | S | CH₃ | 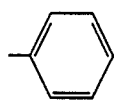 phenyl | ortho | 91 |
| II-3 | O | S | CH₃ | 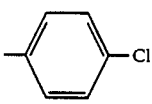 4-chlorophenyl | ortho | 139 |
| II-4 | O | S | CH₃ | 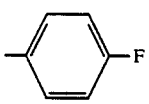 4-fluorophenyl | ortho | 135 |

Starting materials of the formula (IV) Example (IV-1)

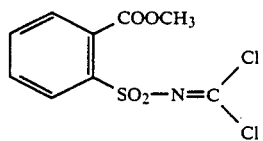

135 g (1 mol) of sulphuryl chloride are added dropwise to a mixture of 27 g (0.085 mol) of dimethyl N-(2-methoxycarbonyl-phenylsulphonyl)-imino-dithiocarbonate and 200 ml of chloroform in such a way that the internal temperature does not exceed 55° C. The complete reaction mixture is stirred at 60° C. for a further hour and the reaction product is then isolated by fractional distillation.

22 g (91% of theory) of N-(2-methoxycarbonyl-phenylsulphonyl)-isocyanide dichloride of boiling point 184° C. at 0.3 kPa are obtained.

The compounds of the formula (IV) shown above in Table 2 can be prepared analogously to Example (IV-1).

Starting compounds of the formula (VI)

Example (VI-1)

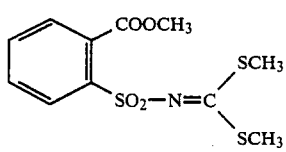

First 11.2 g (0.1 mol) of 1,4-diazabicyclo-[2,2,2]-octane - dissolved in 50 ml of methylene chloride - and then 11.7 g (0.05 mol) of 2-methoxycarbonylbenzenesulphonyl chloride - dissolved in 50 ml of methylene chloride - are added dropwise at 0° C. to 7.4 g (0.05 mol) of dimethyl imino-dithiocarbonate in 100 ml of methylene chloride. The temperature is then allowed to increase to 20°–25° C. and the mixture is subsequently stirred for 18 hours. The reaction mixture is then washed once with dilute hydrochloric acid and twice with water. After evaporating the methylene chloride phase, the residue is triturated with alcohol.

12.5 g (78.3% of theory) of dimethyl N-(2-methoxycarbonyl-phenylsulphonyl)-imino-dithiocarbonate are obtained in the form of colorless crystals of melting point 96° C.

The compounds of the formula (VI) shown above in Table 3 can be prepared analogously to Example (VI-1).

Use examples

In the following use examples, the compound shown below is referred to as the comparison substance:

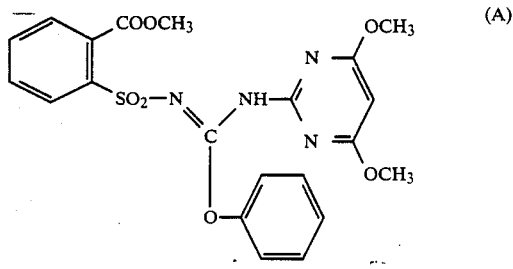

N'-(2-Methoxycarbonyl-phenylsulphonyl)-N"-(4,6-dimethoxypyrimidin-2-yl)-O-phenyl-isourea (known from EP-A 173,957).

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient in doing this to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

The active compounds according to the invention shown a very good herbicidal activity in this test. For example, in this test, in comparison with the known compound (A), the compound according to Preparation Example (2) shows better tolerability towards cultivated plants, such as, for example, wheat, and stronger action against weeds, such as, for example, Chenopodium, Abutilon, Ipomoea and Portulaca.

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound in such a way as to apply the particular amounts of active compound desired per unit area. The concentration of the spray liquor is chosen in such a way that the particular amounts of active compound desired are applied in 2,000 l of water/ha. After three weeks, the degree of damage to the plants is rated in % damage in comparison to the development of the untreated control. The figures denote:

0% = no action (like untreated control)

100% = total destruction

The compounds according to the invention show a very good herbicidal activity in this test. For example, in this test, in comparison with the known compound (A), the compounds according to Preparation Examples (2), (3), (4) and (8) show better tolerability towards cultivated plants, such as, for example, wheat, and stronger action against weeds, such as, for example, Chenopodium, Ipomoea, Portulaca, Veronica and Viola.

It will be appreciated that the instant specification and claims are set forth by way of illustration and not limitation, and that various modifications and changes may be made without departing from the spirit and scope of the present invention.

What is claimed is:

1. A sulphonyliso(thio)urea of the formula

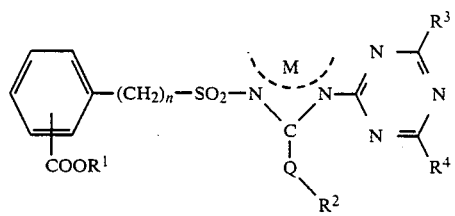

in which

M stands for hydrogen or a sodium, potassium, magnesium or calcium equivalent, n stands for the numbers zero or 1, Q stands for oxygen or sulphur, $R^1$ stands for methyl, ethyl, propyl, isopropyl, butyl, isobutyl, sec.-butyl, 2-fluoro-ethyl, 2-chloro-ethyl, 2-methoxy-ethyl or 2-ethoxyethyl, $R^2$ stands for a phenyl radical, which is optionally substituted by one or two radicals from the group consisting of fluorine, chlorine, bromine, iodine, cyano, nitro, hydroxyl, carboxyl, $C_1$–$C_3$-alkoxycarbonyl, $C_1$–$C_4$-alkyl, trifluoromethyl, hydroxymethyl, methoxy-carbonylmethyl, phenyl-$C_1$–$C_3$-alkyl, cyclohexyl, $C_1$–$C_3$-alkoxy, trifluoromethoxy, $C_1$–$C_3$-alkylthio, trifluoromethylthio, dimethylamino, amino, acetamido, methylaminocarbonyl, formyl, acetyl, benzoyl, phenyl, hydroxyphenyl, phenoxy (which is optionally substituted by chlorine and/or trifluoromethyl), phenylamino, phenylazo, pyridoxy (which is optionally substituted by chlorine and/or trifluoromethyl), or for naphthyl;

$R^3$ stands for methyl, ethyl, trifluoromethyl, methoxy, ethoxy, difluoromethoxy or trifluoroethoxy, and $R^4$ stands for methyl, methoxy, ethoxy, difluoromethoxy or trifluoroethoxy.

2. A compound according to claim 1, in which
M stands for hydrogen,
n stands for zero,
Q stands for sulphur,
$R^1$ stands for methyl or ethyl,
$R^2$ stands for phenyl which is optionally substituted by a substituent from the group consisting of fluorine, chlorine, methyl and methoxy,
$R^3$ stands for methyl or methoxy, and
$R^4$ stands for methoxy with the proviso that the $COOR^1$ group is situated in the ortho-position.

3. A compound according to claim 1,
in which
M stands for hydrogen,
n stands for 1,
Q stands for sulphur,
$R^1$ stands for methyl or ethyl,
$R^2$ stands for phenyl which is optionally substituted by a substituent from the group consisting of fluorine, chlorine, methyl and methoxy,
$R^3$ stands for methyl, ethyl, trifluoromethyl, methoxy or difluoromethoxy, and
$R^4$ stands for methoxy of difluoromethoxy with the proviso that the $COOR^1$ group is situated in the ortho-position.

4. A compound according to claim 1, wherein such compound is N'-(4-methoxy-6-methyl-s-triazin-2-yl)-N'-(2-methoxycarbonyl-phenylsulphonyl)-S-(4-hydroxyphenyl)-isothiourea of the formula

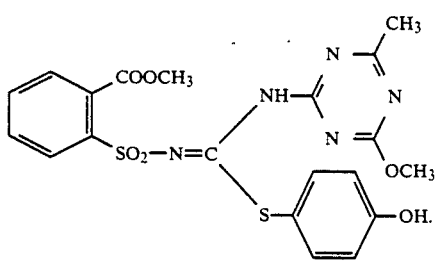

5. A compound according to claim 1, wherein such compound is N'-(4-methoxy-6-methyl-s-triazin-2-yl)-N'-(2-methoxycarbonyl-phenylsulphonyl)-S-(4-methoxyphenyl)-isothiourea of the formula

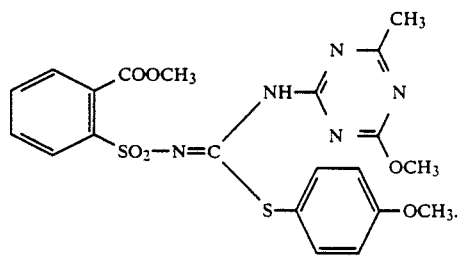

6. A compound according to claim 1, wherein such compound is N'-(4-methoxy-6-methyl-s-triazin-2-yl)-N'-(2-methoxycarbonyl-phenylsulphonyl)-S-(4-fluorophenyl)-isothiourea of the formula

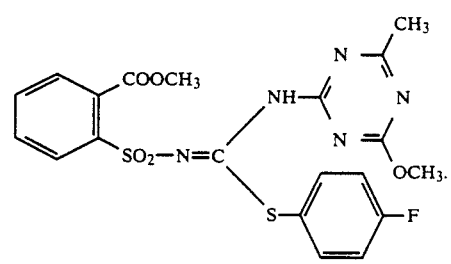

7. A compound according to claim 1, wherein such compound is N'-(4-methoxy-6-methyl-s-triazin-2-yl)-N'-(2-methoxycarbonyl-phenylsulphonyl)-S-(3,4-dichlorophenyl)-isothiourea of the formula

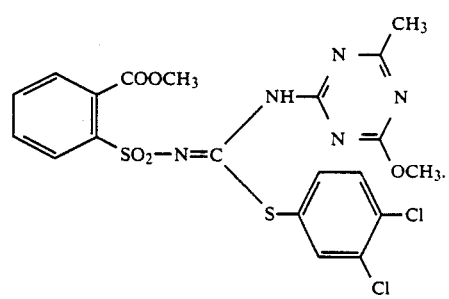

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is
N'-(4-methoxy-6-methyl-s-triazin-2-yl)-N'-(2-methoxycarbonyl-phenylsulphonyl)-S-(4-hydroxyphenyl)-isothiourea,
N'-(4-methoxy-6-methyl-s-triazin-2-yl)-N'-(2-methoxycarbonyl-phenylsulphonyl)-S-(4-methoxyphenyl)-isothiourea,
N'-(4-methoxy-6-methyl-s-triazin-2-yl)-N'-(2-methoxycarbonyl-phenylsulphonyl)-S-(4-fluorophenyl)-isothiourea, or
N'-(4-methoxy-6-methyl-s-triazin-2-yl)-N'-(2-methoxycarbonyl-phenylsulphonyl)-S-(3,4-dichlorophenyl)-isothiourea.

* * * * *

UNITED STATES PATENT AND TRADEMARK OFFICE
CERTIFICATE OF CORRECTION

PATENT NO. : 4,923,505

DATED : May 8, 1990

INVENTOR(S) : Hans-Jochem Riebel, et al

It is certified that error appears in the above-identified patent and that said Letters Patent is hereby corrected as shown below:

Col. 27, line 46          Delete "with the proviso that the $COOR^1$ group is situated in the ortho-position"

Signed and Sealed this

Twenty-fourth Day of December, 1991

Attest:

HARRY F. MANBECK, JR.

*Attesting Officer*          *Commissioner of Patents and Trademarks*